United States Patent
Namias et al.

(10) Patent No.: US 11,481,896 B2
(45) Date of Patent: Oct. 25, 2022

(54) ANGIOGRAPHIC DATA ANALYSIS

(71) Applicant: Brainomix Limited, Oxford (GB)

(72) Inventors: Rafael Namias, Oxford (GB); Olivier Joly, Oxford (GB); Eric Greveson, Oxford (GB)

(73) Assignee: Brainomix Limited

( * ) Notice: Subject to any disclaimer, the term of this patent is extended or adjusted under 35 U.S.C. 154(b) by 6 days.

(21) Appl. No.: 16/899,300

(22) Filed: Jun. 11, 2020

(65) Prior Publication Data

US 2020/0394793 A1  Dec. 17, 2020

(30) Foreign Application Priority Data

Jun. 12, 2019 (GB) ..................................... 1908440

(51) Int. Cl.
*G06T 7/00* (2017.01)
*G06T 7/11* (2017.01)
(Continued)

(52) U.S. Cl.
CPC .......... *G06T 7/0012* (2013.01); *G06K 9/6215* (2013.01); *G06T 5/30* (2013.01);
(Continued)

(58) Field of Classification Search
CPC . G06T 7/0012; G06T 7/11; G06T 5/30; G06T 5/50; G06T 2207/10081;
(Continued)

(56) References Cited

U.S. PATENT DOCUMENTS

| | | | | |
|---|---|---|---|---|
| 7,953,262 B2* | 5/2011 | Suryanarayanan | ..... | G06T 7/162 382/128 |
| 2004/0258296 A1* | 12/2004 | Bruijns | ..... | G06T 7/00 382/154 |

(Continued)

FOREIGN PATENT DOCUMENTS

GB    1908440.9    7/2019

OTHER PUBLICATIONS

Bogunovic et al. "Automatic Identification of Internal Carotid Artery from 3DRA Images." 32nd Annual International Conference of the IEEE EMBS, Aug. 31, 2010, pp. 5343-5346 (Year: 2010).*

(Continued)

*Primary Examiner* — Jon Chang
(74) *Attorney, Agent, or Firm* — Tumey L.L.P.

(57) ABSTRACT

A method of analysing data from an angiographic scan that provides three-dimensional information about blood vessels in a patient's brain, the method comprising the steps of:
  processing the data (26) to produce a three-dimensional image;
  extracting the system of blood vessels inside the skull, so as to obtain a vessel mask (28);
  skeletonising (30) the vessel mask with a thinning algorithm to produce a skeleton mask
  performing a central plane extraction;
  analysing (32) the skeleton mask to identify voxels that have more than two neighbours, indicating a fork, bifurcation or branch;
  detecting the most proximal location of each of the three main supplying arteries of the head in the skeleton mask to identify starting positions; and then
  starting from each starting position in turn, and walking along the line representing the corresponding blood
(Continued)

vessel to detect (34) a plurality of anatomical markers within the network of blood vessels.

12 Claims, 4 Drawing Sheets

(51) Int. Cl.
    *G06K 9/62*     (2022.01)
    *G06T 5/30*     (2006.01)
    *G06T 5/50*     (2006.01)
    *G06V 10/34*     (2022.01)

(52) U.S. Cl.
    CPC .................. *G06T 5/50* (2013.01); *G06T 7/11* (2017.01); *G06V 10/34* (2022.01); *G06T 2207/10081* (2013.01); *G06T 2207/30016* (2013.01); *G06T 2207/30101* (2013.01); *G06T 2207/30104* (2013.01); *G06T 2207/30204* (2013.01); *G06T 2211/404* (2013.01); *G06V 2201/031* (2022.01)

(58) Field of Classification Search
    CPC . G06T 2207/30016; G06T 2207/30104; G06T 2207/30204; G06T 2211/404; G06T 2207/30101; G06T 7/12; G06K 9/6215; G06K 9/469; G06K 9/44; G06K 2209/051; G06K 9/6202; A61B 6/501; A61B 6/5217; A61B 6/481; A61B 6/032; A61B 6/504; G06V 2201/031; G06V 10/34; G06V 10/751; G06V 10/426

See application file for complete search history.

(56) References Cited

U.S. PATENT DOCUMENTS

| | | | |
|---|---|---|---|
| 2007/0019846 A1* | 1/2007 | Bullitt | .................. G06T 7/0014 382/128 |
| 2014/0355858 A1 | 12/2014 | O'dell | |
| 2020/0085318 A1* | 3/2020 | Ezer | ........................ G06T 17/00 |

OTHER PUBLICATIONS

Sandowski et al. "Mathematical Morphology Analysis of 3D Mra Images of Human Brain for Estimation of Blood Vessels Parameters." Joint Conference New Trends in Audio & Video and Signal Processing: Algorithms, Architectures, Arrangements and Applications, Sep. 27, 2012, 4 pages (Year: 2012).*

Nouri Anass et al: "3D bifurcations characterization for intra-cranial aneurysms prediction", Progress in Biomedical Optics and Imaging, SPIE—International Society for Optical Engineering, Bellingham, WA, US, vol. 10949, Mar. 15, 2019 (Mar. 15, 2019), pp. 109491T-109491T.

Lauric A et al: "Automated detection of intracranial aneurysms based on parent vessel 3D analysis", Medical Image Analysis, Oxford University Press, Oxford, GB vol. 14, No. 2, Apr. 1, 2010 (Apr. 1, 2010), pp. 149-159.

* cited by examiner

ANGIOGRAPHIC DATA ANALYSIS

CROSS-REFERENCE TO RELATED APPLICATIONS

This application claims the benefit of GB Application No. 1908440.9 filed on Jun. 12, 2019.

STATEMENT REGARDING FEDERALLY SPONSORED RESEARCH DEVELOPMENT

Not Applicable.

BACKGROUND OF THE INVENTION

Field of Invention

The present invention relates to a method for analysing data corresponding to an angiographic image, for example a tomographic image of a patient's head obtained by angiography, to assist a medical professional diagnosing the medical condition of the patient, and identifying suitable treatment. Such an image may be referred to as an angiogram.

Background of the Invention

The invention is particularly suitable for a diagnosis of a patient who has recently had a stroke. There are two different types of stroke: a haemorrhagic stroke, in which there is bleeding within the brain; and an ischaemic stroke in which there is a blockage of a blood vessel which reduces or prevents blood flow to a region of the brain. A haemorrhagic stroke is detectable in a computed tomographic image of the brain because the blood is denser than the brain tissue, and therefore attenuates X-rays to a greater extent; while an ischaemic stroke is detectable in a computed tomographic image of the brain because the cause of the blockage is a blood clot which may be detectable because of its greater X-ray attenuation, and because the region of the brain in which cells have died as a consequence of the lack of oxygen decreases in density towards that of water, and therefore becomes detectable through reduced X-ray attenuation. The present invention is particularly suitable for determining the location of a blood clot in early stages after the onset of an ischaemic stroke, when treatment to remove the blockage can have a significant effect in the subsequent recovery of the patient, in preventing further brain damage.

The invention utilises data obtained by computed tomography. Tomography is a technique for obtaining a cross-sectional image of an object, in particular by measuring X-ray attenuation along multiple paths through the cross-section by scanning a source and an opposed sensor around the object and deducing the cross-sectional image by computation. Along any one path, the observed attenuation is determined by the cumulative attenuation of each successive portion of the object that makes up the path. Although computed tomography was originally envisaged for obtaining two-dimensional images, information about the three-dimensional structure of an object can be obtained by combining information from multiple two-dimensional images in closely spaced planes, or by a performing a scan along a helical path around the object. To obtain a two-dimensional image, the cross-sectional area is broken down into pixels, and the computation calculates attenuation for each pixel. The smaller the pixels the greater the potential resolution of the image, but the more calculation is required, and the more noise will be present in the image; by way of example each pixel may be 1.0 mm square, or 0.5 mm square. To obtain a three-dimensional image, data from multiple two-dimensional images are combined, and the values of attenuation are deduced for "volumetric pixels" usually referred to as "voxels". The height of each voxel (i.e. the dimension orthogonal to the plane of the two-dimensional image) may differ from the spacing between the planes of successive two-dimensional images, for example it may be larger than the spacing so that the calculated attenuation of each voxel incorporates data from a plurality of two-dimensional images. For example each voxel might be between 0.5 mm and 8 mm high, for example 5 mm high. Normally, in a raw CT angiogram each voxel has spatial dimensions 0.5 mm×0.5 mm×0.6 mm.

When a patient who has had an ischaemic stroke arrives in hospital, it is important for decisions on the appropriate treatment to be made both accurately and rapidly, as faster treatment can minimise the amount of brain tissue that is ultimately affected by the stroke. The medical professional ideally needs to know where the blockage of the blood vessel is, where any dead brain tissue is, and which regions of brain tissue can potentially be saved. Although one blood vessel may have been blocked, so depriving one region of brain tissue of oxygen, there may be surrounding regions of the brain that continue to obtain oxygen by perfusion from collateral arteries. It may be possible therefore to treat the patient so as to ensure that these surrounding regions do not deteriorate further, if treatment is provided soon enough. Computed tomography is a comparatively rapid process, as a scan of a patient's head can be performed in just a few minutes.

The images obtained by computed tomography (CT) scanning may be assessed by the medical professional to determine the nature of the stroke. In the case of an ischaemic stroke it would then be common practice to perform a CT angiogram, i.e. to perform angiography, to determine the location of the occlusion or blood clot. This involves performing computed tomography after administration of a bolus of an X-ray contrast material into the blood supply, typically into a vein, in order to identify relatively higher or lower local blood densities. If the ischaemic stroke is due to occlusion of a large blood vessel, the patient may be treated by endovascular treatment, also known as thrombectomy or mechanical clot removal. If this treatment is to be carried out, it is of fundamental importance first to accurately locate the position of the clot, and this can be achieved by angiography, as it will show up as a "contrast stop", that is to say an absence of, or sudden decrease in, contrast density beyond a point within a vessel where in the absence of a clot no such sudden change in contrast density would be expected. Mechanical thrombectomies are mostly performed on occlusions located in the large arteries, such as internal carotid arteries (ICA), proximal middle cerebral arteries (MCA), proximal anterior cerebral arteries (ACA), basilar artery, and proximal posterior cerebral arteries (PCA), because these arteries provide the requisite access for thrombectomy devices. Consequently, correctly identifying the vessels in the angiogram is crucial to help the medical professional identify the territory and location of the occlusion, and so to assist the medical professional to select the correct treatment and to plan the intervention on the patient.

However, these arteries follow paths that are three-dimensional, and the interconnections are somewhat complex particularly in the vicinity of the circle of Willis, and indeed the exact positions of the interconnections vary between different patients, so analysing the angiographic images is not straightforward. An improved method for analysing such angiographic images would be desirable.

BRIEF SUMMARY OF THE INVENTION

According to the present invention, in a first aspect, there is provided a method of analysing data from an angiographic scan that provides three-dimensional information about blood vessels in a patient's brain, the method comprising the steps of:

processing the data to produce a three-dimensional image;

extracting the system of blood vessels inside the skull, so as to obtain a vessel mask, that is to say a three-dimensional image that consists only of the blood vessels;

skeletonising the vessel mask with a thinning algorithm to produce a skeleton mask, so each blood vessel is reduced to a line of width one voxel;

optionally performing a central plane extraction, so as to separate the skeleton mask into left and right sides;

analysing the skeleton mask along each blood vessel to identify voxels that have more than two neighbours, indicating a fork, bifurcation or branch, these identified voxels being referred to as branch voxels;

detecting the most proximal location of each of the three main supplying arteries of the head in the skeleton mask, the left and right internal carotid arteries and the basilar artery, to identify starting positions that are most distant from the vertex of the skull; and then starting from each starting position in turn, and walking along the line representing the corresponding blood vessel, noting the locations of branch voxels and the relative orientation of the branch, and thereby detecting a plurality of anatomical markers within the network of blood vessels.

It will be appreciated that the above process enables several different anatomical markers to be located within the image. The exact procedure for detecting an anatomical marker will obviously depend upon the nature of the anatomical marker. Some suitable anatomical markers are:

T-ICA: where the internal carotid artery splits into the MCA and ACA;

A1/A2: where the left and right ACA interconnect, usually through an anterior communicating artery;

M1/M2: where the MCA splits into branches;

M1/P1: where the MCA communicates with the posterior communicating artery (which leads to the PCA); and B/P1: where the basilar artery splits to form the left and right PCAs.

It will be understood that alternative anatomical markers might be identified in addition to, or in place of, these markers.

By way of example the B/P1 marker may be identified by walking up the basilar artery until the highest branch point is reached; the T-ICA marker may be identified by walking up the corresponding ICA to the first branch point. Additional information may be utilised to identify the anatomical markers, for example the orientation of the branch may be taken into account; or there may be an additional requirement that the branch point falls within a predetermined region of interest, the region of interest being determined on the basis of a prior atlas image which may be built for example by hand-annotating the equivalent branch point in multiple CT angiograms from other patients, all the angiograms being in registration with each other, so indicating with high statistical likelihood where to expect the branch point in the common atlas reference space.

The attenuation associated with a voxel is typically measured in Hounsfield units (HU), which gives a linear scale in which the radiodensity of distilled water is 0 HU, while the radiodensity of air is −1000 HU. By way of example the radiodensity of bone will be more than 200 HU, that of a blood clot may be about 60 HU, while that of healthy grey matter brain tissue is about 40 HU.

The step of extracting the system of blood vessels inside the skull, so as to obtain a vessel mask, may be performed by comparison of the angiographic image with a non-contrast CT image which is co-registered with it (i.e. the two images of the patient's skull are in registration with each other), determining the difference between the images. The resulting voxel data may then be further improved by then omitting any voxel for which the data is less than a preset threshold, for example 60 HU. Further post-processing steps may include removal of connected components within the resulting thresholded image, if the components are smaller than a preset volume, such as 4, 10 or 20 voxels.

The step of performing the central plane extraction may be performed by registration of the skeleton mask with a template with a known centre plane.

The overall result of the steps described above is that an image may be displayed that shows the three-dimensional structure of the arteries, and in which the identified anatomical markers are marked in the image. This will assist the medical professional in determining the location of any clot, and determining how it may be removed. Thus as a final stage, the medical professional may carry out the thrombectomy at the location as identified from this display.

BRIEF DESCRIPTION OF THE DRAWINGS

The invention will now be further and more particularly described, by way of example only, and with reference to the accompanying drawings in which.

DETAILED DESCRIPTION OF THE INVENTION

Figure 1:
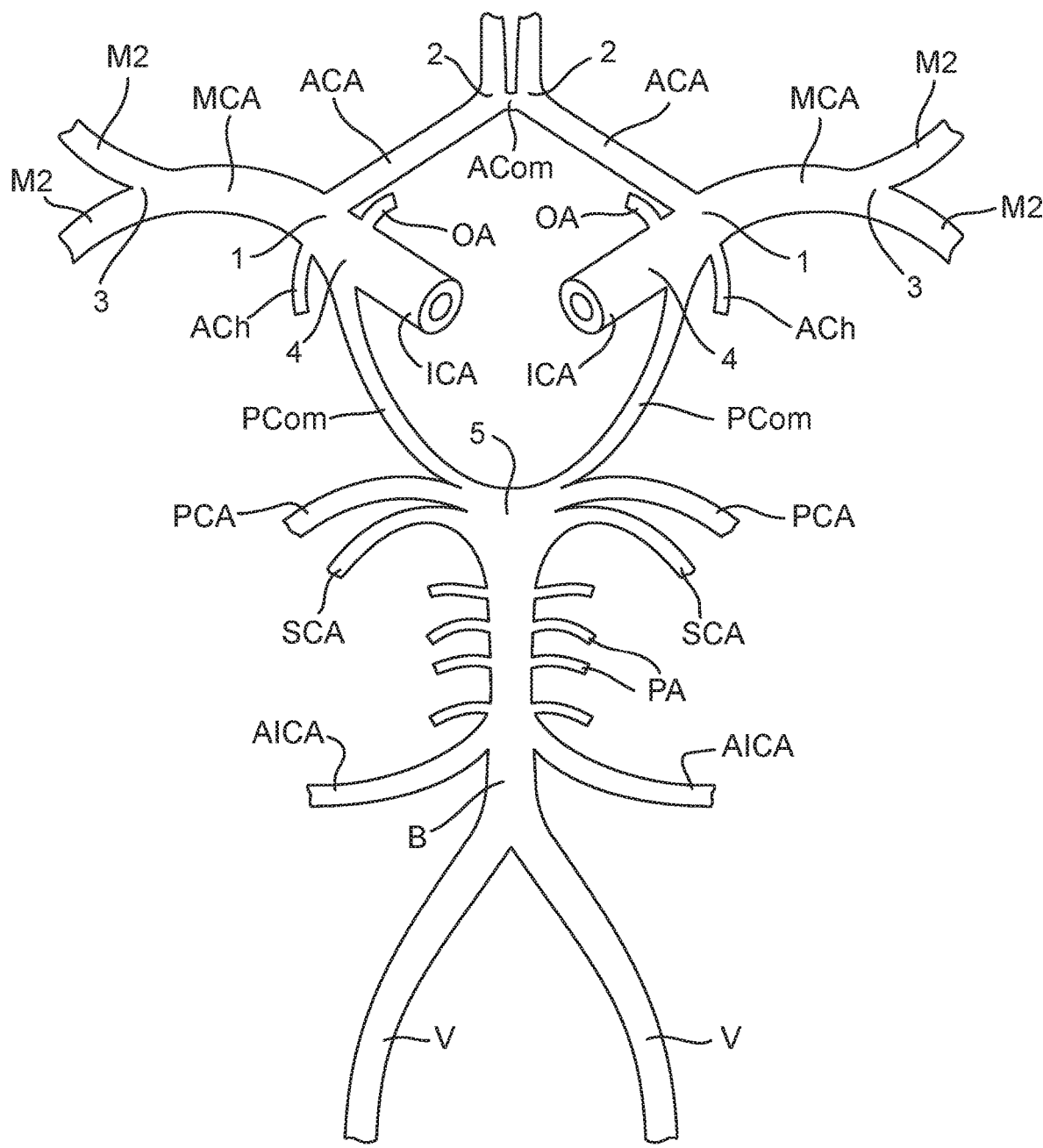
FIG. 1 shows a schematic view of the arteries that provide blood to the brain, the view being at least in part a view from the underside of the brain, showing the circle of Willis.

Referring to FIG. 1, the arteries leading into the brain and those within the brain are to a significant extent symmetrical about the centre plane of the brain. Hence, as a general rule, whatever features are on the left-hand side are also present on the right-hand side in mirror image. Blood is supplied to the brain through three arteries: the basilar artery B, and left and right internal carotid arteries ICA.

The basilar artery B is formed by joining of left and right vertebral arteries V. The basilar artery B extends upward, having a number of arteries leading from it: anterior inferior cerebellar arteries AICA, pontine arteries PA, superior cerebellar arteries SCA, and finally the basilar artery B splits into two posterior cerebral arteries PCA. Each posterior cerebral artery PCA is connected to the corresponding internal carotid artery ICA by a posterior communicating artery PCom.

Each internal carotid artery ICA has a branch which is the ophthalmic artery OA, and then splits to form the middle cerebral artery MCA and the anterior cerebral artery ACA; there is also a branch to the anterior choroidal artery ACh.

The middle cerebral artery MCA subsequently splits to form two branches M2. The left and right anterior cerebral arteries ACA are interconnected by a short artery referred to as the anterior communicating artery ACom.

It will be appreciated that FIG. 1 is a simplified and schematic diagram to indicate the normal way in which the various arteries are interconnected. By way of example, referring now to FIG. 2, this shows a three-dimensional view of these same arteries, in an individual, as viewed from the top. There are some minor differences in labelling: the initial portion of the posterior cerebral artery PCA is labelled P1; the initial portion of the middle cerebral artery MCA is labelled M1; the portions of the anterior cerebral artery ACA before and after the anterior communicating artery ACom are labelled A1 and A2. As compared to the schematic diagram of FIG. 1, it will be appreciated that the arrangement is not exactly symmetrical, and that also that some of the arteries are much less prominent than others. For example the initial portion P1 of the posterior cerebral artery PCA is much more prominent on the left-hand side than on the right (which is not labelled), while the left-hand Pcom (which is not labelled) is much larger than the right-hand PCom.

The method of the present invention enables the locations of several anatomical markers to be identified in the three-dimensional image showing the blood vessels, as obtained by an angiographic scan. In particular the following anatomical markers can be identified, and their locations in the diagram of FIG. 1 are shown by the corresponding reference numerals:

1. T-ICA: where the internal carotid artery ICA splits into the MCA and ACA;
2. A1/A2: where the left and right ACA interconnect, usually through an anterior communicating artery ACom;
3. M1/M2: where the MCA splits into branches;
4. M1/P1: where the MCA communicates with the posterior communicating artery PCom (which leads to the PCA); and
5. B/P1: where the basilar artery splits to form the left and right PCAs.

Having obtained an angiographic image, these locations can be identified using a method along the following lines.
 a) Extract the complete vessel system inside the skull by bringing a non-contrast CT image into registration with the angiographic image, i.e. co-registering the two images, brain masking to exclude any portions of the images that are clearly outside the brain, and subtraction, followed by thresholding at a fixed HU value (e.g. 40 HU or 60 HU). The output is a vessel mask.
 b) Skeletonize the vessel mask with a thinning algorithm (e.g. "A fast parallel algorithm for thinning digital patterns", T. Y. Zhang and C. Y. Suen, Communications of the ACM, March 1984, Volume 27, Number 3), so producing a skeleton mask.
 c) Perform a central plane extraction based on co-registration to a template with a known central plane (e.g. an image where pixels with X values of less than half the image width are on the right side of the brain, in conformity with radiography convention). The skeleton mask now has labels for each foreground pixel of "left" or "right".
 d) Analyse the skeleton mask with starting points on the central plane (i.e. those voxels neighbouring "left" and "right" labels), and iterate over the mask perpendicular to the central plane, looking for forks/bifurcations/branching, for example using the approach in T.-C. Lee, R. L. Kashyap and C.-N. Chu, "Building skeleton models via 3-D medial surface/axis thinning algorithms", Computer Vision, Graphics, and Image Processing, 56(6):462-478, 1994. Voxels at branch points (>2 skeleton mask neighbours) are labelled as hits.
 e) Detect the most proximal location of the three main supplying arteries of the head in the skeleton mask: left and right ICAs, and the basilar artery B. To do this, in our defined reference template image, voxel ranges are labelled for "Left ICA", "Right ICA" or "Basilar". The lowest point (most distant from skull vertex) in the skeleton mask within each of these label ranges is selected accordingly.
 f) Starting from the bottom of the basilar artery B walk through the centre line path upwards and stop on the highest hit. This hit defines the B/P1 anatomical marker 5.
 g) Start from the bottom of the left ICA, move upwards through the skeleton mask until the first hit on the path. This hit defines the left t-ICA marker 1.
 h) Repeat step g for the right ICA.
 i) Starting from the left t-ICA marker 1, walk upwards and centrally along the A1 segment of ACA until the first hit which defines the A1/A2 marker 2.
 j) Starting from the left t-ICA, walk laterally to the left and the right along the M1 centre line path for any hit in the path which creates a bifurcation to the posterior part of the brain, and annotate the hit as a M1/P1 marker 4. The first hit which forks laterally or anteriorly defines the M1/M2 marker 3.
 k) Repeat steps j and k for the right half.

Figure 3:
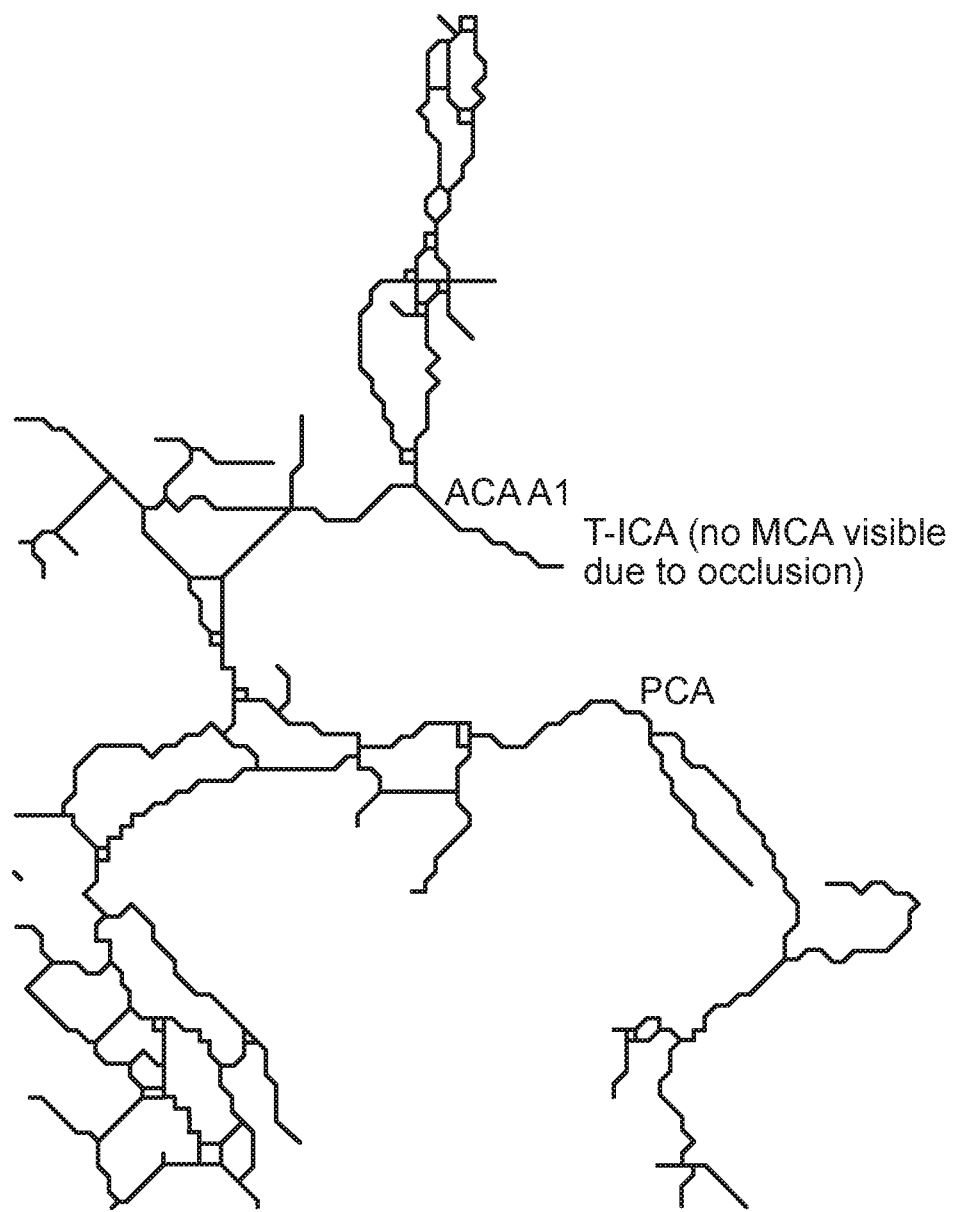
FIG. 3 shows part of a skeleton mask of arteries in a particular patient.

Referring now to FIG. 3, this shows part of a skeleton mask as produced in step (b). This shows an axial two-dimensional view of a three-dimensional skeleton mask. The mask consists of lines of voxels, and it will be appreciated that diagonal gaps of one pixel width between one voxel and the next do not represent breaks in the corresponding artery, but rather are a pixelisation artefact. The image shows the circle of Willis near the centre of the image, and the posterior cerebral artery (PCA) which forms the lower part of the circle of Willis. The left-hand side of the image shows the circle of Willis as complete, leading up to the anterior communicating artery ACA. On the right-hand side of the image, the circle of Willis is incomplete as the middle cerebral artery (MCA) is not visible due to occlusion, and the posterior communicating artery on the right-hand side is therefore not visible either.

In performing the central plane extraction of step (c), the skeleton mask is compared to a template for which the central plane has already been determined. The template may be obtained from a single scan of an individual, generating a skeleton mask from that scan and then determining the central plane of the skeleton mask; or alternatively the template may be produced by averaging skeleton masks obtained from scans of a number of different individuals, and then determining the central plane of the averaged mask.

Figure 2:
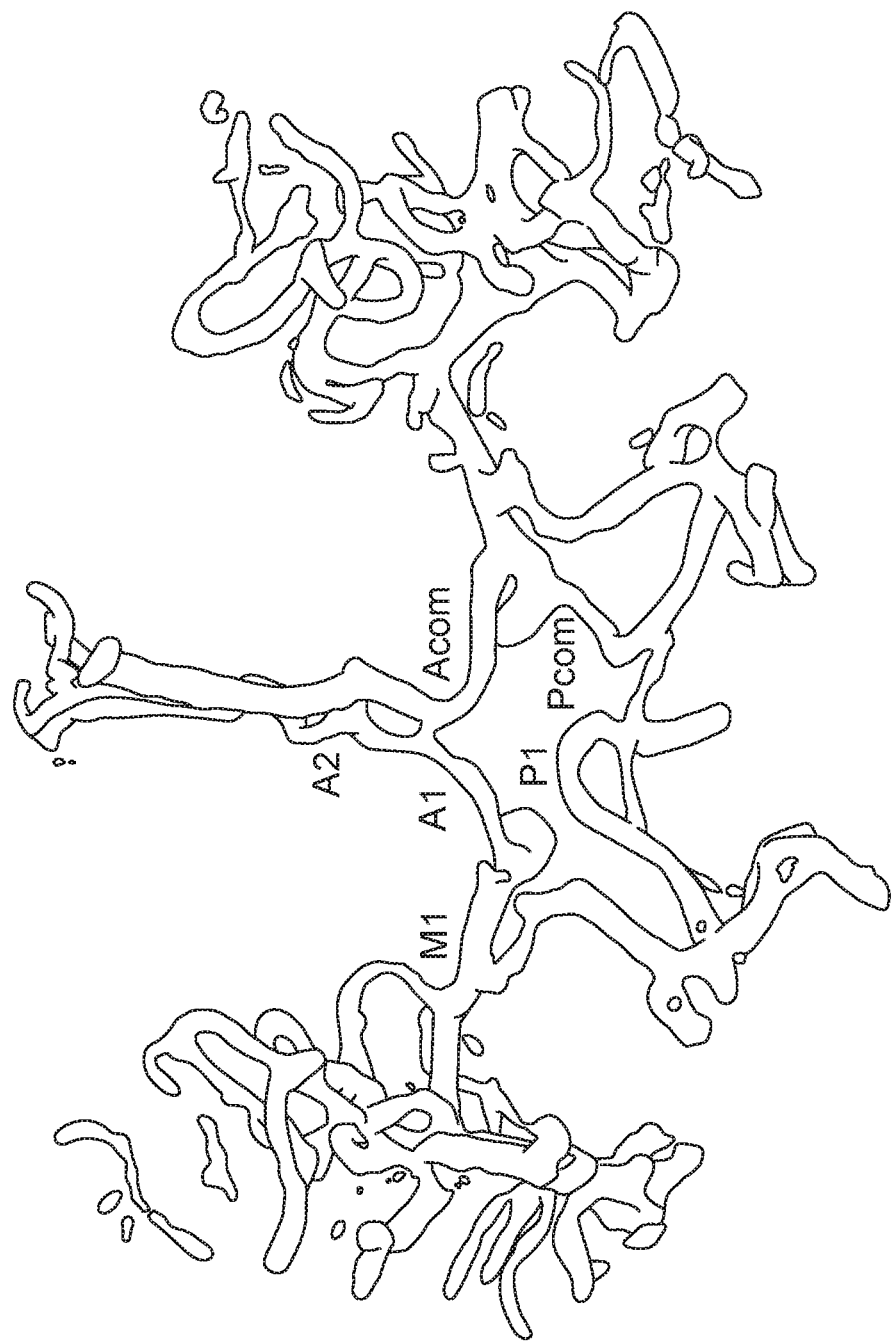
FIG. 2 shows a volume-rendered 3D mesh of the arterial segments around the circle of Willis, in a particular patient.

Steps (f) to (k) may utilise additional information to locate the anatomical markers. In some cases a reference skeleton mask may be used to define regions of interest, that is to say regions in which it is expected that particular anatomical markers will be found. Each search for a branch voxel, i.e. a hit, within a skeleton mask may therefore be carried out within a previously specified region of interest. For example three-dimensional vessel masks as shown in FIG. 2 showing the arteries in the brain can be obtained from angiography scans of multiple people who are not suffering from any brain injury, and can be annotated (for example by a medical expert) with the locations of a number of different anatomical markers in three-dimensional space. Hence it is possible, for each anatomical marker, to deduce a region of that three-dimensional space in which that anatomical marker can be expected to be found, i.e. a region of interest. By way of example by comparing several such annotated angiographic scans, the mean 3-D position of an anatomical marker can be calculated, and also the standard deviation; it would then be expected that in any new scan that the corresponding anatomical marker would be found within say three standard deviations of the mean position.

It will be appreciated that this is only one example of a method of the invention. Although the skeleton mask represents each artery by a line of width only one voxel, information may also be recorded about the diameter of the artery at each position along the line, and about the distance along the flow path. If there is ambiguity about a particular branch voxel or hit, such additional information may enable the ambiguity to be resolved.

Figure 4:
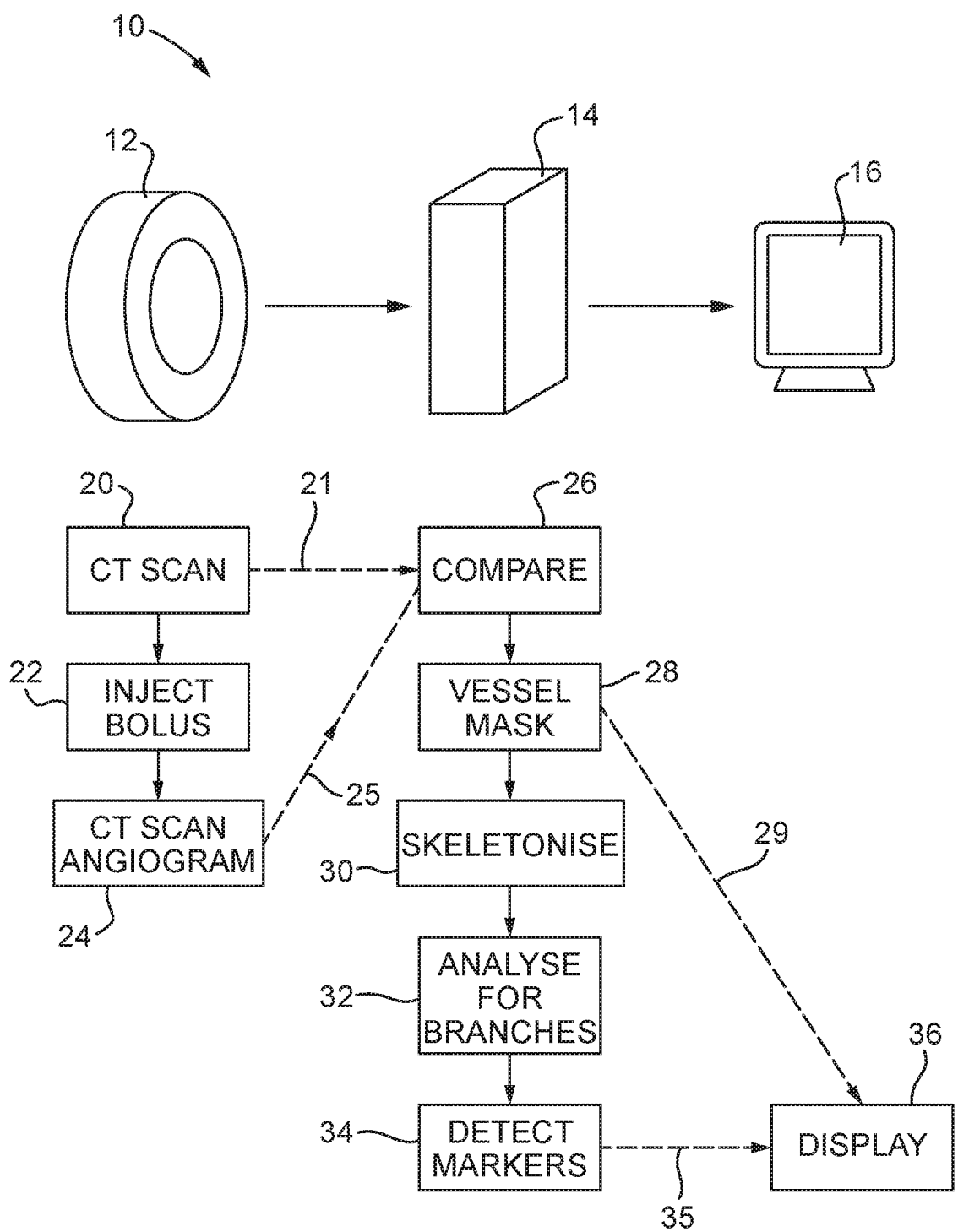
FIG. 4 shows a flow diagram of the process of the invention.

Referring now to FIG. 4, this shows a flow diagram of the process, in three columns, corresponding to the steps performed using corresponding parts of the apparatus 10, represented schematically. The apparatus 10 essentially consists of a scanner 12, which provides data to a computer 14, which provides data to a display 16.

The first step 20 involves performing a scan, which in this example is a CT scan, of the patient's head. Data from that first CT scan, as indicated by the broken line 21, is transferred to the computer 14. The second step 22 is to inject a bolus of contrast material into the patient; and after a sufficient time delay for the contrast material to have circulated into the blood vessels of the brain, the next step 24 is to perform a second scan; because this is a scan which includes contrast material, the resultant image may be referred to as an angiogram. As indicated by the broken line 25, data from this angiographic scan is also transferred to the computer 14.

The computer 14, at step 26, compares the image from the angiographic scan with the image from the initial scan, i.e. comparing the images corresponding to data 21 and data 25, so producing at step 28 a vessel mask such as that shown in FIG. 2, showing the blood vessels in three dimensions. The computer then skeletonises this vessel mask, at step 30, to produce a skeleton mask. The skeleton mask is then analysed at step 32 to identify any branches or bifurcations. The computer then at step 34, by walking along identified major arteries, identifies anatomical markers.

The vessel mask is transferred to the display 16, as indicated by the broken line 29; and the data about the positions of the anatomical markers are transferred to the display 16 as indicated by the broken line 35. As step 36 the display 16 then shows the vessel mask with the identified anatomical markers superimposed at the corresponding positions in the vessel mask. This can assist the medical staff in identifying the nature of the stroke, and the location of any blockage or clot, and determining how best to treat the patient.

What is claimed is:

1. A method of analysing data from an angiographic scan that provides three-dimensional information about a network of blood vessels in a patient's brain, the method comprising the steps of:
    processing the data to produce a three-dimensional image;
    extracting the system of blood vessels inside the skull, so as to obtain a vessel mask comprising a three-dimensional image that consists only of the blood vessels;
    skeletonising the vessel mask with a thinning algorithm to produce a skeleton mask, so each blood vessel is reduced to a line of width one voxel;
    analysing the skeleton mask to identify voxels that have more than two neighbours, indicating a fork, a bifurcation, or a branch, these identified voxels being referred to as branch voxels;
    detecting the most proximal location of each of the three main supplying arteries of the head in the skeleton mask, the left and right internal carotid arteries and the basilar artery, to identify starting positions that are most distant from the vertex of the skull; and then
    starting from each starting position in turn, and walking along the line representing the corresponding blood vessel, noting the locations of branch voxels and the relative orientation of a fork, a bifurcation or a branch, and thereby detecting a plurality of anatomical markers within the network of blood vessels.

2. A method as claimed in claim 1 also comprising displaying the angiographic scan or the vessel mask along with the anatomical markers at the corresponding positions within the angiographic scan or the vessel mask.

3. A method as claimed in claim 1 wherein the step of extracting the system of blood vessels inside the skull, so as to obtain a vessel mask, is performed by comparison of the angiographic image with a non-contrast CT image which is in registration with it, and determining the difference between the images.

4. A method as claimed in claim 3 wherein the voxel data of the differences between the images is further improved by then omitting any voxel for which the data is less than a preset threshold.

5. A method as claimed in claim 4 wherein the preset threshold is 60 HU.

6. A method as claimed in claim 1 further comprising performing a central plane extraction, so as to separate the skeleton mask into left and right sides;
    wherein the step of performing the central plane extraction is performed by registration of the skeleton mask with a template with a known centre plane.

7. A method as claimed in claim 1 wherein the anatomical markers are selected from:
    T-ICA: where the internal carotid artery splits into the MCA and ACA;
    A1/A2: where the left and right ACA interconnect, usually through an anterior communicating artery;
    M1/M2: where the MCA splits into branches;
    M1/P1: where the MCA communicates with the posterior communicating artery; and
    B/P1: where the basilar artery splits to form the left and right PCAs.

8. A method as claimed in claim 7 wherein the B/P1 marker is identified by walking up the line of the basilar artery in the skeleton mask until the highest branch point is reached.

9. A method as claimed in claim 7 wherein the T-ICA marker is identified by walking up the line of an ICA to the first branch point.

10. A method as claimed in claim 1 wherein at least one anatomical marker of the plurality of anatomical markers is identified using, in addition to the skeleton mask, additional data selected from the orientation of the branch, or the width of the branch.

11. A method as claimed in claim 1 wherein at least one anatomical marker of the plurality of anatomical markers is identified using, in addition to the skeleton mask, a requirement that the at least one anatomical marker must lie within a previously-specified region of the skeleton mask.

12. A method as claimed in claim 11 wherein the specified region of the skeleton mask is determined on the basis of a reference skeleton mask.

\* \* \* \* \*